United States Patent [19]

Kaczmarzyk et al.

[11] 4,044,766
[45] Aug. 30, 1977

[54] COMPRESSED CATAMENIAL TAMPONS WITH IMPROVED CAPABILITIES FOR ABSORBING MENSTRUAL FLUIDS

[75] Inventors: Leonard M. Kaczmarzyk; James J. Hlaban, both of Neenah; Leo J. Bernardin, Appleton, all of Wis.

[73] Assignee: Kimberly-Clark Corporation, Neenah, Wis.

[21] Appl. No.: 661,971

[22] Filed: Feb. 27, 1976

[51] Int. Cl.² .................... A61F 13/00; A61F 13/20
[52] U.S. Cl. .................................. 128/285; 128/270; 128/296; 536/87; 536/88; 536/98
[58] Field of Search ........................... 536/87, 88, 98; 128/285, 270

[56] References Cited

U.S. PATENT DOCUMENTS

| 3,379,720 | 4/1968 | Reid | 536/87 |
|---|---|---|---|
| 3,379,721 | 4/1968 | Reid | 536/88 |
| 3,521,638 | 7/1970 | Parrish | 128/284 |
| 3,589,364 | 6/1971 | Dean et al. | 128/285 |
| 3,618,607 | 11/1971 | Ells et al. | 128/285 |
| 3,731,686 | 5/1973 | Chatterjee | 128/285 |

FOREIGN PATENT DOCUMENTS

| 558,280 | 6/1958 | Canada | 128/285 |

Primary Examiner—Ronald W. Griffin
Attorney, Agent, or Firm—Daniel J. Hanlon, Jr.; William D. Herrick; Raymond J. Miller

[57] ABSTRACT

This invention is directed to a compressed catamenial tampon made up of a mass of absorbent fibers having intermixed therein a quantity of carboxymethylcellulose fibers containing free-acid carboxyl radicals and characterized by a high capacity for absorbing and retaining menstrual fluids. These carboxymethylcellulose fibers are modified by heat treatment to shorten the time it takes for such fibers to absorb a specified amount of fluid and thereby more effectively utilize their high capacity. The particular high capacity fibers are defined as carboxymethylcellulose fibers having a degree of substitution in the normally soluble range of about 0.4 to about 2.0 in which a part of the carboxyl groups are in free-acid form with the remainder in salt form.

9 Claims, No Drawings

COMPRESSED CATAMENIAL TAMPONS WITH IMPROVED CAPABILITIES FOR ABSORBING MENSTRUAL FLUIDS

BACKGROUND OF THE INVENTION

The majority of tampons now on the market are made from batts of absorbent fibers such as cotton linters, or blends of cotton with rayon and the like, compressed to a self-sustaining form and to a size adapted for easy insertion into the vaginal tract. While these tampons have been generally acceptable for menstrual protection, their limited absorbent capacity for menstrual fluids combined with poor retentive capabilities for such fluids under normal body pressures often require the user to make frequent, and often premature changes, in order to provide satisfactory service.

Accordingly, attempts have been made to improve performance by adding to the tampon other absorbent materials which have much higher fluid capacity and better retention capabilities than the conventional fibers mentioned above, thus permitting tampons to be worn for a longer time period between changes.

In the prior art one can find a number of patents suggesting the use of various of the so-called "super" absorbent materials for such purposes. Representative of such patents are U.S. Pat. No. 3,589,364 Dean et al, U.S. Pat. No. 3,618,607 Ells et al, U.S. Pat. No. 3,669,103 Harper et al, U.S. Pat. No. 3,670,731 Harmon, U.S. Pat. No. 3,678,031 Schoggen, U.S. Pat. No. 3,723,413 Chatterjee et al, and U.S. Pat. No. 3,731,686 Chatterjee. While the teachings in each of these patents appear to arrive at materials which when incorporated in tampon structures do provide higher fluid capacity and retention, these highly desirable characteristics are apparently achieved at the expense of a reduced absorbency rate, i.e. the tampon has a reduced ability to immediately and rapidly take up fluid from the time of insertion into the vagina. A common disadvantage of this prior art appears to be that while the tampons described therein do show an increased total capacity and some retention improvements, these properties often are not efficiently utilized because of an inability to rapidly draw the fluids into the tampon resulting in fluid bypass or early leakage. Thus, even though such tampons are effective when flow is light and/or slow, and the fluid has time to penetrate into the interior of the tampon; at other times when flows are heavy and/or fast, the tampon is unable to completely contain the fluids which will then bypass the tampon and result in undesirable early failure necessitating change without utilizing potential capacity. In such event, the addition of these high capacity materials is detrimental rather than helpful. While this problem apparently is alleviated in some of the teachings by suggesting structures in which the high capacity fibers are segregated from the more economical conventional fibers which do accept fluids readily, or layered between layers of such conventional fibers, no real solution has been found with respect to improving the performance of tampons in which the high capacity fibers are substantially evenly distributed throughout the tampon structure and which is generally more desirable from a manufacturing standpoint.

Another surprising finding was that even though some laboratory bench tests for measuring potential performance of these tampon products, which tests are designed to simulate in-use conditions and use vagina-like devices and various other test procedures described in the prior art, seemed to indicate that the performance of these high capacity materials would be satisfactory in use, actual clinical tests by users during menstrual periods found otherwise.

This invention is directed to a compressed tampon of absorbent fibers having distributed throughout the tampon structure a quantity of high capacity fibers modified to improve their absorbency rate for menstrual fluids without substantially decreasing total capacity and fluid retention capabilities, which tampons show an improved performance in actual use.

SUMMARY OF THE INVENTION

The high capacity fibers employed in this invention are carboxymethylcellulose fibers having a degree of substitution in the range of about 0.4 to about 2.0, which is within the normally soluble range, and in which a part of the carboxyl groups are in free-acid form with the remainder of the carboxyl groups being in salt form. The improved absorbency rate is obtained by heat-treating the fibers sufficiently to shorten the time required to absorb a specified amount of fluid to 41 minutes or less. For purposes of this invention, absorbency time is defined as the number of minutes it takes for one gram of the material compressed to the 5cc mark in a 10cc BD multifit glass syringe to absorb a 0.9% NaCl solution up the 5cc mark. The absorbency time for the above-defined fibers is lowered, i.e. the absorbency rate becomes faster, as more heat energy is applied to the fibers in a pretreatment process. Satisfactory performance for tampons containing such fibers is attained when the absorbency time is lowered to 41 minutes or less. Peak performance is obtained when the absorbency time is lowered to about 25 minutes. Lowering the time below 25 minutes maintains high performance but does not further improve performance to the degree which one might ordinarily expect. The preferred density range for compressed tampons containing such fibers is 0.55 grams to about 0.75 grams per cubic centimeter, although the invention is applicable to densities in the range of about 0.35 grams to about 0.85 grams per cubic centimeter.

Tampons using the free-acid radical containing carboxymethylcellulose fibers defined herein in amounts ranging from 5% to about 30% of such fibers by weight of the tampon are contemplated. Various mixtures of absorbent fibers other than the rayon and cotton fibers set forth in the specific examples are also contemplated.

DESCRIPTION OF THE PREFERRED EMBODIMENTS AND COMPARISONS WITH PRIOR ART

The method of manufacturing the free-acid radical containing carboxymethylcellulose fibers used in this invention, which fibers are subsequently heat-treated in accordance with the teachings of this invention, is well known in the art and no claim is made to its manufacture per se.

Briefly, the first step in this known method is to slurry cellulose fibers in an aqueous solution of an inert organic solvent such as isopropanol. The preferred starting fibers are cotton linters, but other cotton fibers, as well as cellulosic fibers from other well-known sources including regenerated cellulose may be used. The slurried cellulosic fiber is reacted with a water soluble alkali-metal hydroxide, preferably sodium hydroxide, to form alkali cellulose. The resulting alkali cellulose is then reacted with an etherifying agent to supply the carboxyl radical and obtain the alkali-metal salt of carboxymethylcellulose. A suitable etherifying agent is monochloracetic acid. The alkali cellulose is etherified to a degree of substitution in the range of about 0.4 to about 2.0 which normally is in the soluble range for carboxymethylcellulose. A degree of substitution of about 0.6 to 0.8 is preferred. A higher degree of substitution, e.g. 2.0, may also be used, of course, but is less economical and is not necessary to obtain the desired results.

A method for modifying the alkali-metal salt of carboxymethylcellulose to convert a portion of the carboxyl radicals to the free-acid form may be found in U.S. Pat. No. 3,379,720 to Reid. As described therein, after the alkali metal salt of carboxymethylcellulose is washed free of the etherifying reactant, it is again slurried in a similar aqueous solution of an inert organic solvent as previously described. The solution is then acidified by a strong acid, such as nitric or hydrochloric acid, to a pH of between about 3 and 5 and held at the reduced pH for a suitable period to permit the conversion of a desired percent of the carboxyl groups from their original salt form to free-acid form. Free-acid groups in the amount of about 5 to 40% are satisfactory. After acidification, excess liquid is drained off and the material washed, usually to a pH of about 6 to 7.5. The material is then air-dried at elevated temperatures.

In general, the lower the pH during this conversion process, the higher is the ratio of free-acid groups to salt groups. Ratios may be varied from about 0.2/1 to about 0.7/1.

A specific example of carboxymethylcellulose material suitable for use in this invention and prepared in the above manner to contain the free-acid radical had a degree of substitution of being about 0.6 to 0.7 and a COOH/COONa ratio of about 0.6 to 1. When tested for its rate of absorbency, the fibers of this example were found to have an absorbency time of about 53 minutes.

The apparatus and steps for carrying out the absorbency rate test were as follows:

ABSORBENCY RATE TEST

The test apparatus consists of a 10cc glass syringe (BD multifit), a plunger for compressing material placed in the syringe, a fluid reservoir, a device to hold the syringe in an upright position in the fluid reservoir, and a timer.

One gram of the fibrous material to be tested is weighed out and placed in the 10cc syringe.

The plunger is used to compress the one gram of material inside the syringe to the 5cc mark, yielding a density of 0.2 g/cc.

A colored 0.9% saline solution is placed in the reservoir and the syringe adjusted in the holder to extend into the solution up the 0cc mark when the syringe is standing upright. The reservoir should be sufficiently large so that the removal of a few milliliters of fluid does not change the depth significantly.

With the fiber in place in the syringe and the syringe lowered into the reservoir until the 0cc mark is at the fluid level, the timer is started.

The time in minutes for the fluid to reach the 1, 2, 3 etc. cc marks on the syringe is recorded.

After the rate of absorbency was determined, these modified carboxymethylcellulose fibers were used to make fibrous batts about 1½ inches × 3½ inches × ½ inch in size and containing 4.2 grams of a blended mixture of 40% rayon, 30% cotton linters and 30% of the free-acid radical containing carboxymethylcellulose fibers. These batts were compressed to round-nosed tampons about ½ inch in diameter and 1½ inches in length and a density of 0.75 grams/cc. The finished tampons were subjected to a number of tests including both bench tests and clinical in-use tests and compared to control tampons of similar density but comprising 60% cotton linters and 40% rayon and devoid of high capacity fibers.

One bench test which was carried out was to measure absorbent capacity using what is known in the art as a Syngina, and which comprises a tubular rubber sheath fixed inside a glass jacket to form an artificial vagina. The sheath is set at an angle of about 30° to the horizontal and the tampons are positioned inside the membrane with the lower end about 2.5 inches from the lower opening of the sheath with the withdrawal string extending outside of the opening. Hydrostatic pressure is then put on the outside of the sheath which collapses around the tampon. Colored test fluid (0.9% NaCl solution) is then admitted to the top of the tampon by a hypodermic needle at a rate slow enough to prevent puddling. When fluid drips from the lower end of the sheath it is assumed that the tampon is saturated and that the absorbent capacity is reached. The tampon is then removed, and the total weight of test fluid remaining in the tampon is calculated.

For this test, the control 4.2 gram tampon which did not contain high capacity fibers absorbed an average of 9.0 grams of test while the modified tampon containing the above-defined free-acid radical containing carboxymethylcellulose fibers having the 53 minute absorbency time absorbed 18.3 grams of test fluid.

This bench test appeared to indicate that because of the improved capacity the latter tampon would be superior in performance during actual use as compared to the control tampon.

However, when the same tampons were tested in actual use, it was found that approximately the same number of the tampons partly comprised of the carboxymethylcellulose fibers with the 53 minute absorbency time failed early as did unmodified tampons.

Early failure is defined as a tampon which permits menstrual fluid to bypass the tampon before 5 hours of use and at the time of bypass has less than 10 grams of menstrual fluid absorbed.

Thus while bench tests showed that the tampon containing the carboxymethylcellulose fibers with the 53 minute absorbency time had potentially higher capacity for saline fluids, this potential capacity was not effectively utilized to absorb menstrual fluids in actual use. Examination of the used tampons indicated that the menstrual fluid did not penetrate into the tampon to any extent, and this may have accounted for their early failure.

Another batch of the same free-acid containing carboxymethylcellulose fibers having the original absorbency time of 53 minutes noted above were heated for 60 minutes at 130° C. and when measured for absorbency after heating registered a 25 minute absorbency time. Still another batch was heated for 75 minutes at 130° C. and after heating, this batch tested at 16 minutes on the absorbency time scale. These heat-treated fibers were then incorporated in tampons in the 30% amount noted for the previously tested high capacity fibers which had the slower 53 minute absorbency time.

The artificial vagina tests for the tampons containing the 25 minute and 16 minute fibers came out at 16.0 and 15.1 grams respectively, indicating that additional heating reduced absorbent capacity somewhat, but such capacity was still substantially higher than the 9 gram capacity of conventional tampons of similar weight. However when these tampons were tested in use there was a 46% and 39% reduction respectively in the number of tampons classified as early failures, when compared to the control tampons. The remaining tampons in these test groups which did not fail early also showed a significant increase in the total amount of menstrual fluid absorbed as compared to these control tampons which did not fail early.

It is clear from the above that the absorbency time as measured in bench tests, rather than total capacity as measured in bench tests, is the critical factor in determining whether or not a tampon will show improved performance in actual use.

In additional tests, more of the free-acid containing carboxymethylcellulose fibers with the original 53 minute absorbency time were heat treated to improve the absorbency time from 53 minutes to 41 minutes and to 20 minutes respectively and then each of these were incorporated in 4.2 gram tampons comprised of 40% cotton linters, 40% rayon fibers and 20% of the heat-treated high capacity fibers and compressed to a size of about ¾ inch diameter and 1¾ inches in length, or a density of about 0.55 grams/cubic centimeter. Syngina tests showed these less dense tampons to have a total absorbent capacity of 15.5 and 14.6 grams respectively. There was a 32% and 17% reduction in early failures compared to control tampons of the same density, and a 23% and 24% increase in the grams of exudate absorbed in comparison to control tampons.

In order to check and compare these findings with somewhat similar high capacity fibers found in the prior art, some additional tests were run. Carboxymethylcellulose fibers in which all the carboxyl groups were in sodium salt form, having a degree of substitution of about 0.8, were heated at 130° for 20 hours, which is in the range taught in the Chatterjee U.S. Pat. No. 3,731,686, and subjected to the same bench and in-use tests previously described. In the absorbency time test for these fibers, no absorbency time could be recorded since no measurable amount of fluid was absorbed in the syringe. Additional heat treatment of the fibers yielded no change in the test results.

In the Syngina test, absorbent capacity for tampons containing 20% of these latter fibers and compressed to a density of 0.55 grams/cc was measured at 11.8 grams. The number of early failures was found to be 137% more compared to the unmodified control tampons. Overall performance was therefore found to be less satisfactory for tampons containing these latter fibers than for control tampons of similar weight.

What is claimed is:

1. A compressed catamenial tampon comprised of a mixture of absorbent fibers in which a selected amount of said absorbent fibers are carboxymethylcellulose fibers having a degree of substitution in the range of 0.4 to 2.0 with at least a portion of the carboxyl radicals present being in free-acid form and the remainder of the carboxyl radicals present being in the alkali-metal salt form and in which said carboxymethylcellulose fibers are characterized by an absorbency time of less than about 41 minutes, said absorbency time being the number of minutes it takes for one gram of said carboxymethylcellulose fibers compressed to the 5cc mark in a 10cc BD multifit glass syringe to absorb a 0.9% NaCl solution up to the 5cc mark.

2. The tampon of claim 1 wherein said free-acid carboxyl radicals comprise a minor portion of the carboxyl radical present.

3. The tampon of claim 1 which the ratio of free-acid carboxyl radicals to the salt form carboxyl radicals is from about 0.2/1 to about 0.7/1.

4. The tampon of claim 1 in which the ratio of free-acid carboxyl radicals to the salt form carboxyl radicals is about 0.6/1.

5. The tampon of claim 1 wherein said carboxymethylcellulose fibers are present in the amount of about 5% to 30% by weight.

6. The tampon of claim 5 wherein the remainder of said absorbent fibers are selected from the group consisting of rayon fibers and cotton fibers.

7. The tampon of claim 1 wherein said tampon is compressed to a density of between about 0.35 to about 0.85 grams per cubic centimeter.

8. The tampon of claim 1 wherein said tampon is compressed to a density of between about 0.55 grams to about 0.75 grams per cubic centimeter.

9. The tampon of claim 1 wherein said absorbency time is about 25 minutes.

* * * * *